United States Patent [19]
DeCarlo, Jr. et al.

[11] Patent Number: 5,716,412
[45] Date of Patent: Feb. 10, 1998

[54] IMPLANTABLE ARTICLE WITH ABLATED SURFACE

[75] Inventors: Alfred F. DeCarlo, Jr., Stamford; Douglas G. Noiles, New Canaan, both of Conn.

[73] Assignee: Johnson & Johnson Professional, Inc., Raynham, Mass.

[21] Appl. No.: 724,493

[22] Filed: Sep. 30, 1996

[51] Int. Cl.$^6$ ................................................ A61F 2/28
[52] U.S. Cl. ................................................ 623/16; 623/66
[58] Field of Search ........................... 623/11, 16, 18, 623/19, 20, 22, 23, 66

[56] References Cited

U.S. PATENT DOCUMENTS

| | | | |
|---|---|---|---|
| 4,272,855 | 6/1981 | Frey | 623/18 |
| 4,549,319 | 10/1985 | Meyer | 623/22 |
| 4,608,052 | 8/1986 | Van Kampen et al. | 623/18 |
| 4,624,673 | 11/1986 | Meyer | 623/16 |
| 4,673,409 | 6/1987 | Van Kampen | 623/23 |
| 4,846,839 | 7/1989 | Noiles | 623/18 |
| 4,865,603 | 9/1989 | Noiles | 623/18 |
| 5,246,530 | 9/1993 | Bugle et al. | 156/643 |
| 5,258,098 | 11/1993 | Wagner et al. | 156/645 |
| 5,507,815 | 4/1996 | Wagner et al. | 623/16 |

OTHER PUBLICATIONS

Buser, D. et al., "Influence of surface characteristics on bone integration of titanium implants. A histomorphometric study in miniature pigs," *Journal of Biomedical Materials Research*, vol. 25, 889.

The Omniflex® AD, CP Titanium Arc Deposited Femoral Stem Series, Osteonics Corp., Allendale, N.J. (1992).

3M™ Ultrapore™ Porous Surface, A solution for osteolysis?, 3M Health Care (1993).

*Primary Examiner*—David Isabella
*Attorney, Agent, or Firm*—Nutter, McClennen & Fish, LLP

[57] ABSTRACT

An implantable article includes a textured bone engaging surface having a surface texture pattern formed by a plurality of furrows separated by ridges that are integral with the base material from which the article is formed. The furrows are formed by ablating in the surface a series of intersecting holes. The side walls of the furrows have scalloped edges. The ablating energy can be applied by techniques such as laser ablation and hydrojet ablation.

18 Claims, 4 Drawing Sheets

IMPLANTABLE ARTICLE WITH ABLATED SURFACE

BACKGROUND OF THE INVENTION

This invention relates to implantable articles, such as joint prostheses, having an integral, textured bone engaging surface, and to methods for producing such articles.

There are known to exist many designs for and methods for manufacturing implantable articles, such as bone prostheses. Bone prostheses include components of artificial joints, such as elbows, hips, knees, and shoulders. An important consideration in the design and manufacture of virtually any implantable bone prosthesis is that the prosthesis be adequately affixed to bone after implantation within the body. In many instances it is important to implant the prosthesis without the use of bone cement and the like.

There are three generally accepted criteria for successful biological fixation of implantable articles within bone. First, the prostheses must be in contact with sound bone. Second, the prostheses must be in a close fit within a prepared cavity within bone. Third, there must be no perceptible motion (micromotion) between the prostheses and the bone under cyclic load bearing conditions. Recent attempts have been made to achieve optimal fixation by utilizing textured bone-engaging surfaces which encourage bone ingrowth.

Early designs of implantable articles relied upon the use of cements, such as polymethylmethacrylate, to anchor the implant. The use of such cements can have some advantages, for instance by providing an immediate and secure fixation that does not develop free play and lead to erosion of the joining bone faces postoperatively. However, the current trend is to use these cements to a lesser extent because of their tendency to lose effectiveness over time and due to the possibility that the cements will contribute to wear debris within a joint.

Recently, implantable bone prostheses have been designed so as to encourage the growth of hard tissue (i.e., bone) to be in intimate contact with the implant. The interaction of newly formed hard tissue in and around a textured surface of the implantable bone prosthesis has been found to provide good fixation of prostheses within the body. A greater degree of bone fixation can usually be achieved where bone engaging surfaces of an implantable bone prosthesis are more porous or irregular.

Porous or irregular surfaces can be provided in implantable articles by a variety of techniques. In some instances irregular surface patterns or surface features are formed in an implantable bone prosthesis by processing techniques such as casting, embossing, chemical etching, milling or machining. See, for example, U.S. Pat. Nos. 4,549,319 and 4,624,673. One drawback to using such techniques to provide irregular bone ingrowth surfaces on implantable bone prostheses is the significant amount of processing time required. These processing operations lead to delays in obtaining the finished product and significantly increase the cost of manufacturing the device.

Pore-forming surfaces can be formed on implantable bone prostheses by sintering small metal particles or powders to a surface of the prosthesis in a random pattern. Wire-based pads or grids can also be fused to implantable bone prostheses to provide a texture or surface relief features. A drawback of such techniques is that the components added to form the textured surface can become dislodged from the substrate of the prosthesis. Dislodgement of these components compromises the fixation mechanics of the implant and can contribute to the formation of wear debris. Further, the sintering step required to fuse texture-forming components to bone prostheses relies upon high temperature processing that could diminish the mechanical properties of the prostheses, distort the dimensions of the prostheses, and/or alter other properties of the materials from which the prostheses are made.

Additional techniques that are used to prepare textured surfaces for implantable articles, such as bone prostheses, include the use of laser energy to alter the surface of the implantable article. For example, U.S. Pat. Nos. 4,608,052; 4,673,409; and 5,246,530 teach various techniques for using a laser to form a plurality of discrete holes in the bone engaging surface of bone prostheses. The bone prostheses formed according to methods taught by these references have relatively regular surface features.

There is thus a need for implantable articles, such as bone prostheses, that have bone engaging surfaces that optimize successful biological fixation and that promote bone ingrowth. Accordingly, it is an object of the invention to provide an implantable article having a bone engaging surface that will achieve a close fit within a patient and promote considerable bone ingrowth. It is another object to provide a textured, bone engaging surface on an implantable article that will reduce stress on subsequent bone ingrowth. It is a further object to provide bone prostheses having textured, bone engaging surfaces that are integral with the bone prostheses. It is also an object to provide an economical method by which the bone engaging surface of implantable article may be textured. Yet another object is to provide a method of forming on an implantable article a textured bone-engaging surface without adversely affecting the metallurgical properties of the article. These and other objects will be apparent to those of ordinary skill in the art upon review of the following disclosure.

SUMMARY OF THE INVENTION

The present invention provides implantable articles, such as bone prostheses, having an integral, textured bone engaging surface formed by a pattern of alternating furrows and ridges. Adjacent furrows are separated by a ridge which is integral with the base material of the prosthesis. Continuous ridges separate adjacent furrows, and the ridges are integral with the bone engaging surface. Preferably, each furrow has scalloped side walls formed by a series of intersecting holes. These holes can be cylindrical or conical and may have generally spherical bottoms. The depth of each furrow, and height of each ridge, is in the range of about of 200 to 1000 microns.

The furrows can be formed in the bone engaging surface in a linear or non-linear fashion. Moreover, the furrows can be formed on irregularly shaped surfaces (e.g., a stepped surface) of the implantable article.

The textured bone engaging surface is formed by ablation of selected portions of the surface, preferably in a pattern of a series of intersecting holes. This pattern forms furrows that are separated by raised, integral ridges in which the sidewalls of the ridges are scalloped. During the ablation process, the ablation apparatus and/or the article itself is manipulated and repositioned in a predetermined manner to form the desired pattern. Ablation can be effected by a variety of techniques capable of selectively removing material from the surface of the article in a desired pattern. Exemplary techniques include laser ablation and hydrojet ablation.

As a consequence of applying laser energy to the surface of the metallic body to form the textured surface pattern, according to one embodiment of the invention, molten metal is ejected from the portion of the body within which the textured pattern is formed. At least a portion of this ejecture typically is deposited on the surface adjacent the furrow from which the ejecture emanates. The ejecture can be allowed to remain adhered to the surface (i.e., the ridges) or it can be removed.

Alternatively, the furrows can be formed through a removable mask which captures the ejecture and which prevents the ejecture from solidifying upon the ridges or elsewhere on the bone-engaging surface of the article. The ejecture is removed upon the removal of the mask.

In one embodiment, furrows can be formed by placing intersecting holes adjacent to one another, in a side-by-side orientation or in an overlapping side-by-side orientation. This enables the formation of a furrow wider than the diameter of a single hole without increasing the radius of the scalloped edges of the ridges.

DETAILED DESCRIPTION OF THE INVENTION

Figure 1:
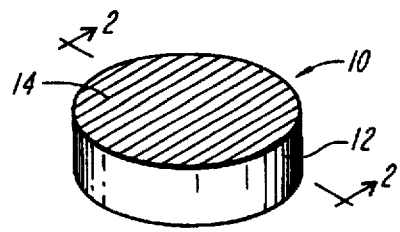
FIG. 1 is a perspective view of an article having a textured surface formed according to the present invention.
Figure 2:
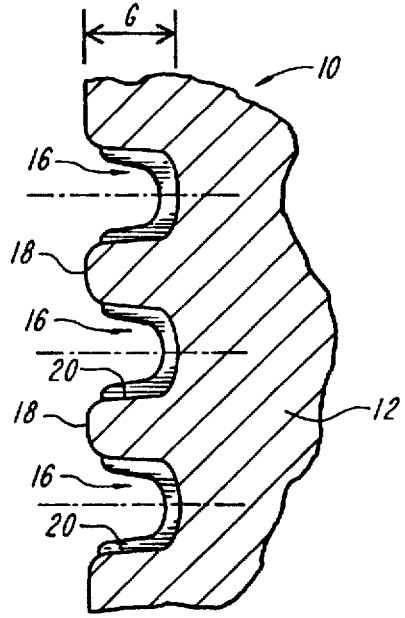
FIG. 2 is a sectional view of the article shown in FIG. 1 at lines 2—2 in FIG. 3.
Figure 3:
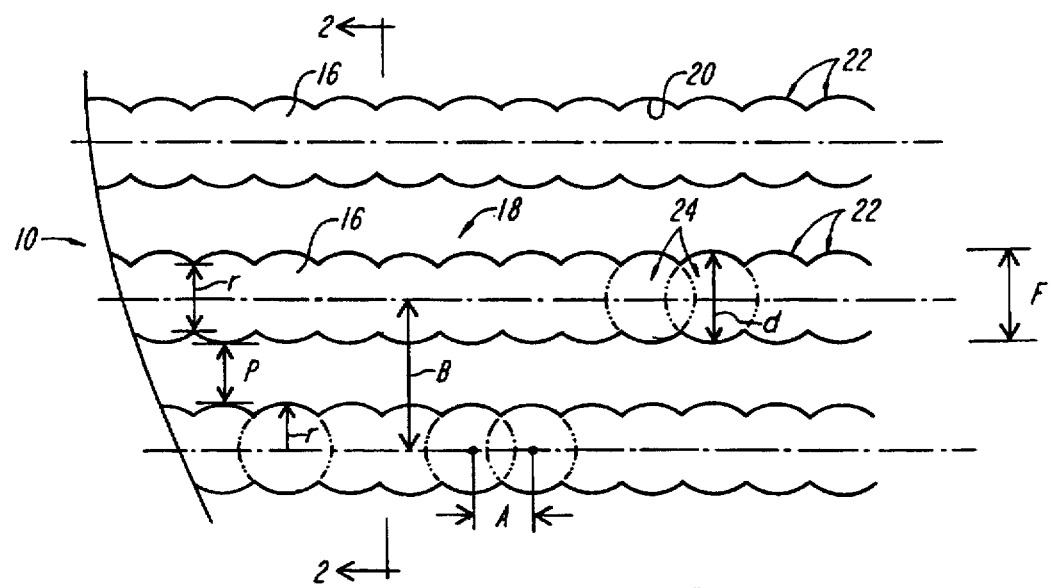
FIG. 3 is a detail, top view of the portion of the article shown in FIG. 1.

As shown in FIGS. 1 through 3, an implantable article 10 includes a metallic body 12 having a bone engaging surface 14. The bone engaging surface 14 represents a textured region. FIGS. 2 and 3 further illustrate that the bone engaging surface comprises a plurality of furrows 16 separated by raised ridges 18. Each furrow has sidewalls 20 formed with scalloped edges 22. The scalloped edges 22 contribute a varying surface pattern to the bone engaging surface, yielding a bone engaging surface that encourages bone ingrowth and that enables good fixation of the implant within the bone. These textural features also impart properties to enable the article to resist shear in two directions.

The furrows 16 are formed by ablating the body 12 in a series of intersecting holes 24. The holes can be cylindrical or conical and may have generally spherical bottoms.

Furrows 16 may extend linearly or non-linearly. Examples of non-linearly oriented furrow patterns include curvilinear furrow patterns and zig-zagging furrow patterns. The scalloped edges 22, as noted above, are formed by a series of segments of intersecting holes, with each hole having a nominal radius (r) and a nominal diameter (d). The distance (A) between adjacent round holes in the same furrow is greater than the nominal radius and less than the nominal diameter of a hole. Generally, this distance is in the range of about 120 to 900 microns. Moreover, the distance (B) between the centers of holes in adjacent furrows is in the range of about 300 to 1600 microns.

The dimensions of the bone engaging surface can vary depending upon the requirements of a given implantable article. Generally, however, the depth of the furrows and the height of the ridges is about 200 to 1000 microns. Similarly, the width of the ridges, at their widest portions, is in the range of about 100 to 750 microns. The width of the furrows is in the range of about 200 to 1500 microns. The sidewalls that define the ridges may be straight or tapered in the vertical direction. Tapered walls preferably are constructed such that a furrow is wider at a top portion thereof than at a base portion thereof.

Various dimensions of the furrows and ridges can be described with reference to FIGS. 2 and 3. The distance (A) between the centers of adjacent holes in the same furrow typically is in the range of about 1.2 to 1.8 times greater than the nominal radius (r), or about 120 to 900 microns. The distance (B) between the centers of adjacent holes in adjacent furrows can typically be the sum of the nominal diameter of a hole (d) and the smallest distance (P) between the outer edges of holes in adjacent furrows. The value of B usually is in the range of about 300 to 1600 microns. The value for the nominal diameter (d) of holes preferably is on the range of about 200 to 1500 microns. The value for P (smallest distance between the outer edges of holes in adjacent furrows) preferably is in the range of about 100 to 600 microns. The depth (G) of the holes that form the furrows preferably is in the range of about 200 to 1000 microns.

Figure 4:
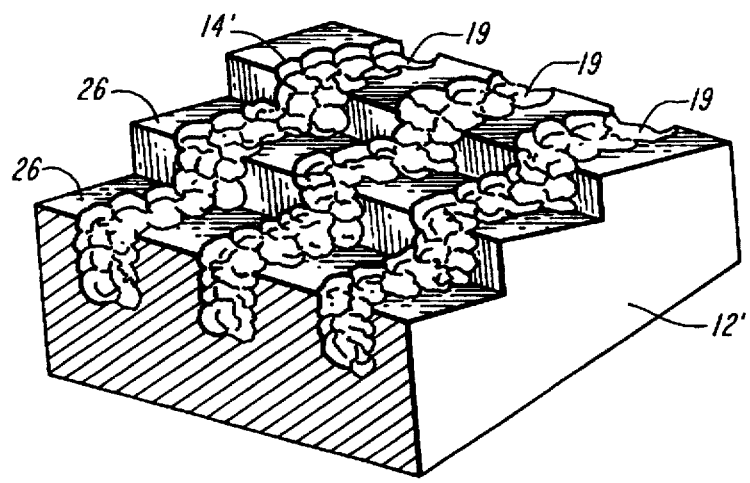
FIG. 4 is a perspective view of an article having a stepped bone-engaging surface with furrows formed therein.

Further, as illustrated in FIG. 4, the pattern 19 of furrows and ridges can be formed on a non-planar surface 21 of an article. In one embodiment this pattern 19 may be disposed on a surface 12' having a bone engaging surface 14' formed by a plurality of stepped plateaus 26. FIG. 4 also illustrates that the furrows disposed in the article may be formed by placing holes side-by-side in an overlapping or adjacent orientation to create a furrow wider than the diameter of a single hole.

Figure 10:
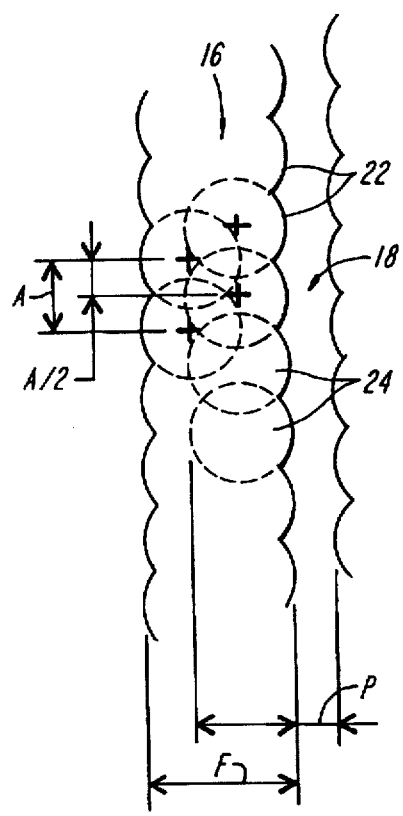
FIG. 10 is a schematic view of an alternative construction of the furrows formed according to the present invention.
Figure 11:
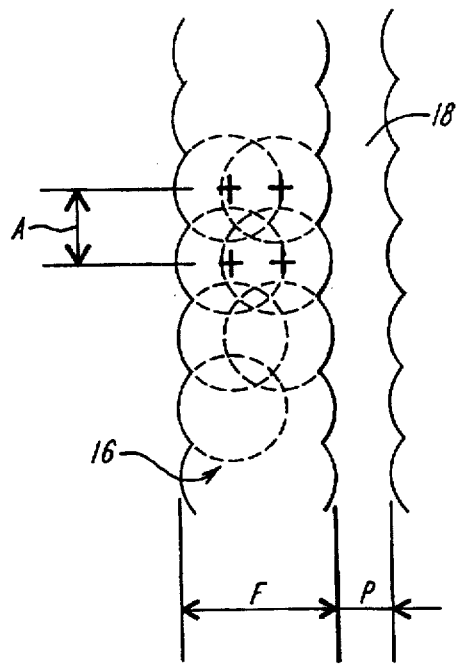
FIG. 11 is a schematic view of an alternative construction of the furrows formed according to the present invention.

FIGS. 10 and 11 further illustrate the side-by-side overlapping orientation of holes to form a furrow having a wider width (F). Such a structure is advantageous because it enables the formation of a wider furrow without increasing the radius of the scalloped edges of the ridges. As illustrated, the dimensions described above with respect to FIGS. 2 and 3 are maintained. In this embodiment, the value of dimension F is greater than the diameter of a single hole, but remains in the range of about 200–1500 microns.

The average volume porosity of surface ablated parts preferably is about 30 to 90%. Also, the volume of space defined by the furrows is greater than the volume of space defined by the ridges.

The textured surface can be formed on a variety of bioimplantable articles including joint prostheses, dental implants, spinal implants, and the like. Exemplary joint prostheses include, but are not limited to, acetabular cups, hip stems, knee femoral components, and tibial components.

Figure 5:
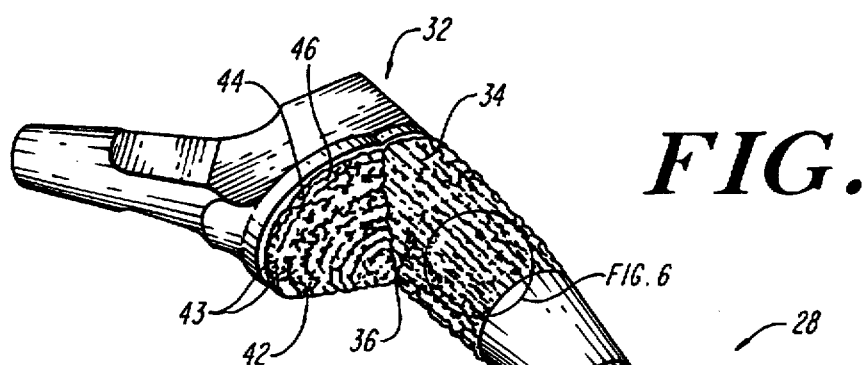
FIG. 5 is a perspective view of a femoral stem component of a hip prosthesis having a textured, bone engaging surface on a portion thereof.
Figure 6:
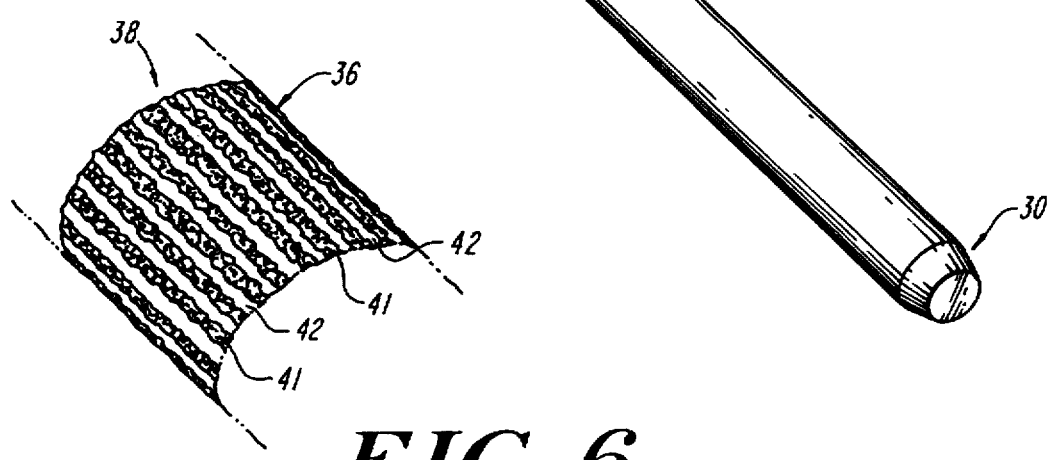
FIG. 6 is a detailed view of a portion of the textured surface of the femoral shown in FIG. 5.

FIG. 5 illustrates a hip joint femoral stem 28, which is an example of one type of article upon which the textured bone engaging surface may be formed. Such a femoral stem is described in co-pending U.S. patent application Ser. No. 08/583,225, filed Jan. 4, 1996 and entitled "Method and Apparatus for Fitting a Prosthesis to Bone." Femoral stem 28 includes distal and proximal ends 30, 32. The metaphyseal region 34, disposed between the distal and proximal ends 30, 32, is an area of the hip stem upon which the fixation to existing bone, and thus good bone ingrowth, is important. As shown in FIG. 5, a textured bone engaging surface 36 is formed upon the metaphyseal region 34. FIG. 6 illustrates, in detail, that the textured bone engaging surface includes a region 38 having vertically oriented furrows 41 and ridges 40. Adjacent to region 38 is region 42, formed by stepped plateaus 43 which has furrows and ridges 44, 46 which diverge from a distal portion 48 of region 42.

Figure 7:
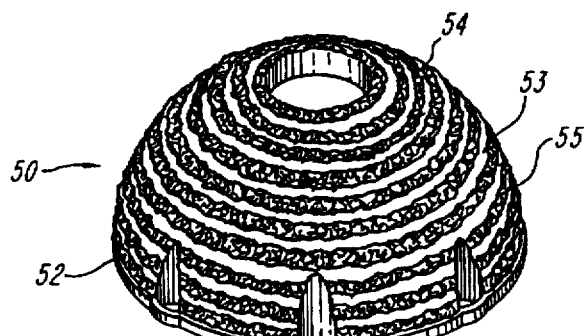
FIG. 7 is a perspective view of an acetabular cup of a hip prosthesis having furrows formed laterally in a portion of the bone engaging surface thereof.
Figure 8:
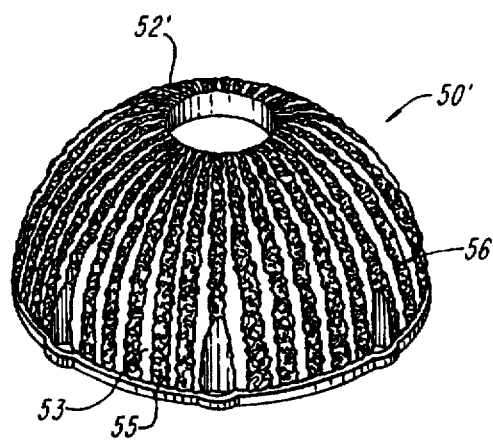
FIG. 8 is a perspective view of an acetabular cup of a hip prosthesis having furrows formed longitudinally in a portion of the bone engaging surface thereof.

FIG. 7 illustrates an acetabular cup 50 having a bone engaging surface 52. A laterally-oriented pattern 54 of ridges 53 and furrows 55 is formed on a portion of bone engaging surface 52. FIG. 8 illustrates an alternative embodiment of an acetabular cup 50' having a bone engaging surface 52'. A longitudinally-oriented pattern 56 of ridges 53 and furrows 55 is formed on a parting bone engaging surface 52'.

Figure 9:
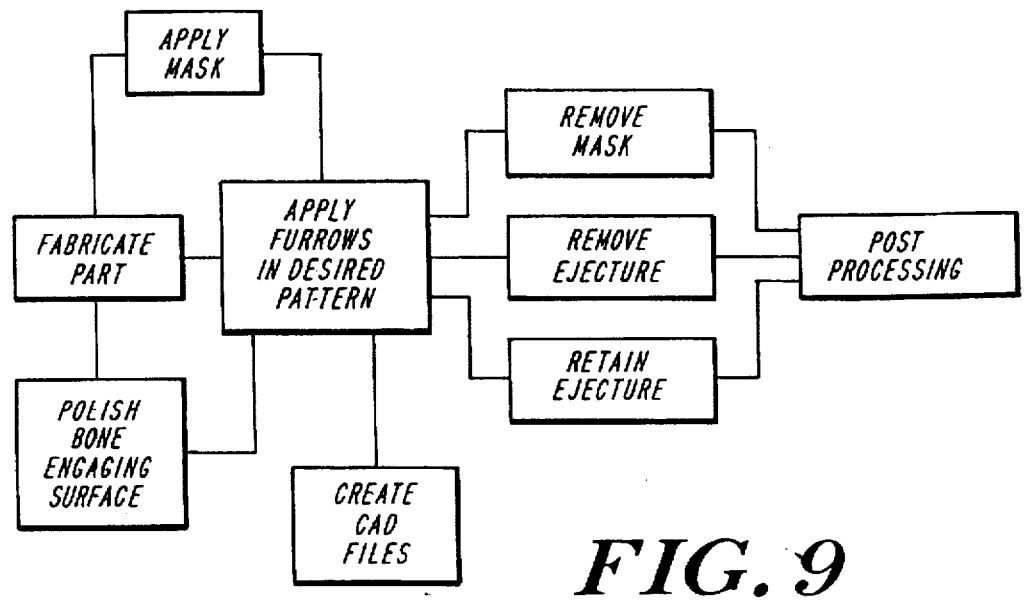
FIG. 9 is a flow chart illustrating a process for forming a textured bone engaging surface according to the present invention.

FIG. 9 is a flow chart illustrating the basic process for forming a textured surface on implantable articles according to the present invention. A metallic implanted article is first fabricated according to known techniques. The article may be treated to reduce or eliminate the amount of ejecture that adheres to the article during a surface texturing process. The surface treatment can involve applying a mask to the article. The mask typically is in the form of a template having a pattern of openings through which the laser beam can be directed. The mask preferably is made of an energy-dissipating material. One example of such a material is a copper foil tape. Alternatively, the article may be polished to create a surface that is of sufficient reflectivity to reduce the amount of ejecture adhering to the article, or toughened to increase the amount of ejecture adhering to the article.

It is known that computer aided design (CAD) files can be programmed to control the path and activity of the laser to achieve virtually any desired pattern for the surface texture. The CAD files preferably are used in conjunction with CNC machines. One of ordinary skill in the art will readily appreciate that the desired tool path can be programmed to achieve a desired surface texture pattern on a virtually unlimited number of parts, including those having complex surfaces.

Once the CAD file is established, it is utilized to direct the ablating energy upon the bone engaging surface of the article in a desired pattern to create the desired surface texture by ablating portions of the surface. In a preferred embodiment a series of furrows, which may be substantially parallel, is formed. Each furrow is formed by ablating the surface of the article in a pattern corresponding to a series of intersecting holes. The result is the formation of a number of furrows, where adjacent furrows are separated by a ridge. The sidewalls of the furrows are defined by scalloped edges, which correspond to the segments of intersecting holes.

After the pattern is completely formed, the article can be treated to remove any loose or unwanted ejecture particles. This can be accomplished by removing the mask, if one is used. If no mask is used, the ejecture can be removed by other, well known techniques. Alternatively, all or most of the ejecture can remain adhered to the article to provide a rougher surface texture. Once these steps have been completed the article can be subjected to any post-processing techniques that are necessary before use, such as polishing, cleaning, packaging, and sterilizing.

The surface ablation can be accomplished by known techniques including laser ablation and hydrojet ablation. The energy is applied to form a series of intersecting holes, thus creating furrows in the surface of the article.

One of ordinary skill in the art will appreciate that a variety of lasers may be successfully used in connection with the present invention to accomplish laser ablation of the surface. Exemplary lasers include YAG lasers (neodymium:yttrium aluminum garnet), carbon dioxide lasers, argon lasers, and neodymium:glass lasers. YAG lasers are among the more preferred, and a suitable YAG laser is the Raytheon SS 500, 400 watt YAG laser. The laser preferably has a power level in the range of about 400–600 watts. The laser preferably has a Pulse Form Network (PFN) of approximately 400–550. The laser pulse width is in the range of about 3 to 8 milliseconds, and preferably is about 5 milliseconds. A pulse rate of about 8 to 12 Hz is preferred as well.

The focal length of a lens used with the laser preferably is sharp to about +0.130 diopter, which focuses the laser a fraction of a millimeter above the surface of the article. Thus, the laser beam is applied to the part slightly out of focus, creating a rougher surface.

In one embodiment, the laser ablation technique can be conducted while the part is shrouded by an inert gas in order to prevent oxidation of the part. A suitable useful inert gas is argon.

The economy which the present laser ablation technique is able to achieve is due, in part, to the speed at which the surface of a part can be treated. At a typical ablation rate of 10 holes per second, it is possible to ablate one square inch of an article in 1.8 minutes. Moreover, the downtime between processing separate parts can be kept to a minimum, e.g., about two minutes.

Ablation can also be effected using a hydrojet technique. This technique, known to those of ordinary skill in the cut, utilizes a high pressure water jet to ablate the surface of the article. The water is in the form of a slurry having fine particles of an abrasive grit. The pressure, diameter, and placement of the water jet is directed and controlled to ablate the surface in a desired pattern.

The ablation apparatus preferably is used in combination with a CNC controlled work station which manipulates the part in a desired manner. Application of the ablation energy to the surface of the part is accomplished in such a way as to yield a hole depth of desired dimensions. The energy is able to form furrows at the rate of about 10 holes per second. Preferably about 1050–2025 holes per square inch are formed by the laser.

The use of the ablation techniques according to the present invention is advantageous and economical. The pattern of furrows formed in the article according to the present invention create an increased surface area on the bone engaging surface of the article. This pattern also provides increased resistance to motion and/or subsidence in a direction normal to the furrows. In a femoral stem, for example, longitudinal furrows prevent rotation while radial furrows prevent subsidence.

In addition to providing a bone-engaging textural geometry which is integral with the body of the article, the invention accommodates the relative strengths of bone versus metal. The strength of the metals used to form the article is many times the strength of bone. Accordingly, an efficient load transferring interdigitated interface between bone and metal should have load carrying members of bone larger than those of metal. The invention accomplishes this by providing the so-called void space in the prosthesis surface to be greater than 50% and to be as great as 85%. Moreover, the formation of a furrowed, textured surface has little or no adverse impact on the metallurgical properties of the article. Heat generated by a laser beam tends not to penetrate deeply into the substrate. On average, the heat affected zone in a titanium part extends to a depth of only about 0.004 inch below the surface. Similarly, the water jet does not have an adverse impact on the properties of the article.

It will be appreciated by those of ordinary skill in the art that the articles upon which the present ablation process can be effected include a variety of metallic, biocompatible materials having high strength and durability and which are suitable to biological implantation. Examples of such materials include biologically compatible metal alloys such as cobalt-chromium alloys, titanium alloys, and stainless steels.

The foregoing description of the invention is presented to indicate the range of construction to which the invention applies. Variations in the physical architecture and dimensions of the implantable articles and the bone engaging surfaces thereof will be apparent to those having ordinary skill in the art based upon the disclosure herein, and such variations are considered to be within the scope of the invention to which patent rights are asserted, as set forth in the claims appended hereto. The entirety of all references herein is hereby incorporated by reference.

What is claimed is:

1. An implantable prosthesis, comprising:
    a body having a bone engaging surface;
    a plurality of furrows formed in at least a portion of the bone engaging surface wherein each furrow has scalloped side walls defined by a series of segments of overlapping holes, each hole having a nominal radius and a nominal diameter; and
    a plurality of ridges separating adjacent furrows, the ridges being integral with the body of the prosthesis.

2. The prosthesis of claim 1 wherein the volume of space defined by the furrows is greater than the volume of space defined by the ridges.

3. The prosthesis of claim 2 wherein the depth of each furrow is in the range of about 200 to 1000 microns.

4. The prosthesis of claim 2 wherein the height of each ridge is in the range of about 200 to 1000 microns.

5. The prosthesis of claim 2 wherein each furrow has a width in the range of about 200 to 1500 microns.

6. The prosthesis of claim 2 wherein each ridge has a width in the range of 100 to 750 microns.

7. The prosthesis of claim 1 wherein the nominal distance between the centers of adjacent, intersecting holes is greater than the nominal radius of the holes and less than the nominal diameter of the holes.

8. The prosthesis of claim 7 wherein the nominal distance between the centers of adjacent, intersecting holes is in the range of about 120 to 900 microns.

9. The prosthesis of claim 1 wherein the distance between the centers of adjacent circles in adjacent furrows in the range of about 300 to 1600 microns.

10. The prosthesis of claim 1 wherein the furrows are non-linear.

11. The prosthesis of claim 10 wherein the furrows are curvilinear.

12. The prosthesis of claim 10 wherein the furrows follow a zig-zag pattern.

13. The prosthesis of claim 1 wherein the bone engaging surface of the prosthesis includes a non-planar surface, and the furrows and ridges are formed upon the non-planar surface.

14. The prosthesis of claim 13 wherein the non-planar surface of the prosthesis is a stepped surface.

15. The prosthesis of claim 1 wherein the body is substantially hemispherical having an outer, bone engaging surface and an inner, non-bone engaging surface.

16. The prosthesis of claim 15 wherein at least a portion of the bone engaging surface has furrows oriented longitudinally therein.

17. The prosthesis of claim 15 wherein at least a portion of the bone engaging surface has furrows oriented latitudinally therein.

18. The prosthesis of claim 1 wherein the body is metallic.

* * * * *